United States Patent [19]

Sting et al.

[11] Patent Number: 5,200,609
[45] Date of Patent: Apr. 6, 1993

[54] RADIANT ENERGY SPECTROSCOPY SYSTEM WITH DIAMOND INTERNAL REFLECTION ELEMENT

[76] Inventors: Donald W. Sting, 358 Turtleback Rd., New Canaan, Conn. 06840; John A. Reffner, 97 Ocean Dr. East, Stamford, Conn. 06902

[21] Appl. No.: 750,201

[22] Filed: Aug. 27, 1991

[51] Int. Cl.⁵ .............................. G01J 31/50
[52] U.S. Cl. .................... 250/226; 250/343; 356/244
[58] Field of Search ............ 356/244, 246, 51; 250/226, 343, 373, 576

[56] References Cited

U.S. PATENT DOCUMENTS

| | | |
|---|---|---|
| 3,393,603 | 7/1968 | Harrick . |
| 3,958,882 | 5/1976 | Gast . |
| 3,963,354 | 6/1976 | Feldman et al. . |
| 4,062,623 | 12/1977 | Suzuki et al. . |
| 4,176,964 | 12/1979 | Knor et al. . |
| 4,602,869 | 7/1986 | Harrick . |
| 4,826,313 | 5/1989 | Schar et al. ............ 356/51 |
| 4,829,186 | 5/1989 | McLachlan et al. ........ 356/51 |
| 4,878,747 | 11/1989 | Sting et al. .. |
| 5,046,854 | 9/1991 | Weller et al. ............ 250/576 |
| 5,093,580 | 3/1992 | Sting . |

OTHER PUBLICATIONS

"Nanosampling internal reflection spectroscopy of solids and liquids" by DeBlase, Spectroscopy, Jun. 1988, pp. 96–107.

Primary Examiner—David C. Nelms
Attorney, Agent, or Firm—Calfee, Halter & Griswold

[57] ABSTRACT

A radiant energy spectroscopy system includes a diamond as a single bounce internal reflection element (IRE). A standard anvil cut diamond can be used as the IRE. Alternatively, a diamond can be specially cut to have a conical, spherical or curved section in the crown and/or in the pavilion and a curved or flat surface portion for the culet and/or table.

19 Claims, 3 Drawing Sheets

RADIANT ENERGY SPECTROSCOPY SYSTEM WITH DIAMOND INTERNAL REFLECTION ELEMENT

FIELD OF THE INVENTION

The present invention relates to a radiant energy spectroscopy system utilizing a diamond as a single bounce internal reflection element (IRE).

BACKGROUND OF THE INVENTION

A specially configured and cut diamond has been used as a multiple bounce internal reflection element. The multiple bounce diamond IRE was configured as a truncated prism having generally trapezoidal side walls, angled end walls and flat top and bottom walls. This multiple bounce diamond IRE was very expensive. Applicants believe that this special multiple bounce diamond IRE has not been commercially successful because of its cost. Applicants are unaware of any diamond being used as a single bounce IRE or of any standard anvil cut diamond being used as a single bounce IRE.

The shapes of most standard cut diamonds include facets. Applicants believe that one would expect the optical imaging properties of the diamond facets to be very poor for the purpose of focusing a beam of energy to and from a simple area. In fact, facets are used to "break up" a visible beam so as to scramble the visible light to give the appearance of "sparkle". This is clearly a contrary purpose to the use described herein.

SUMMARY OF THE INVENTION

The principal object of the present invention is to employ standard anvil cut diamonds as single internal reflection elements in spectroscopy systems. Diamonds as single bounce IREs provide benefits including hardness, chemical resistivity, strength, potential high pressure on the sample and optical clarity.

It is another object of the present invention to provide specially cut diamonds as single bounce IREs in a radiant energy spectroscopy system. By selecting certain angles and face configurations, the optical characteristics of the diamond as a single bounce IRE can be improved. Applicants have found that by increasing the number of facets and making them small and nearly perpendicular to a somewhat spherical wavefront created by high numeric aperture optics (as disclosed in U.S. application Ser. No. 07/622,852, filed Dec. 6, 1990, now U.S. Pat. No. 5,093,580 for "ATR Objective"), a diamond can be made highly useful as a single bounce ATR crystal.

It is still another object of the present invention to utilize a very small diamond as a single bounce IRE in any type of optical system or any orientation. Very small diamonds as single bounce IREs reduce possible distortion of the optical image.

As a probe for radiant energy IR spectroscopy, a diamond with a very small sample contacting surface of less than 10 microns can be used such that the surface defines the area of the sample being analyzed. Such single bounce IRE diamonds having sample contacting surfaces of less than 10 microns allow ultramicroscopy experiments to be performed.

The invention, then, comprises the features hereinafter fully described and particularly pointed out in the claims, the following description an annexed drawings setting forth in detail certain illustrative embodiments of the invention, these being indicative, however, of but a few of the various ways in which the principals of the invention may be embodied.

DETAILED DESCRIPTION OF THE PREFERRED EMBODIMENT

Figure 1:
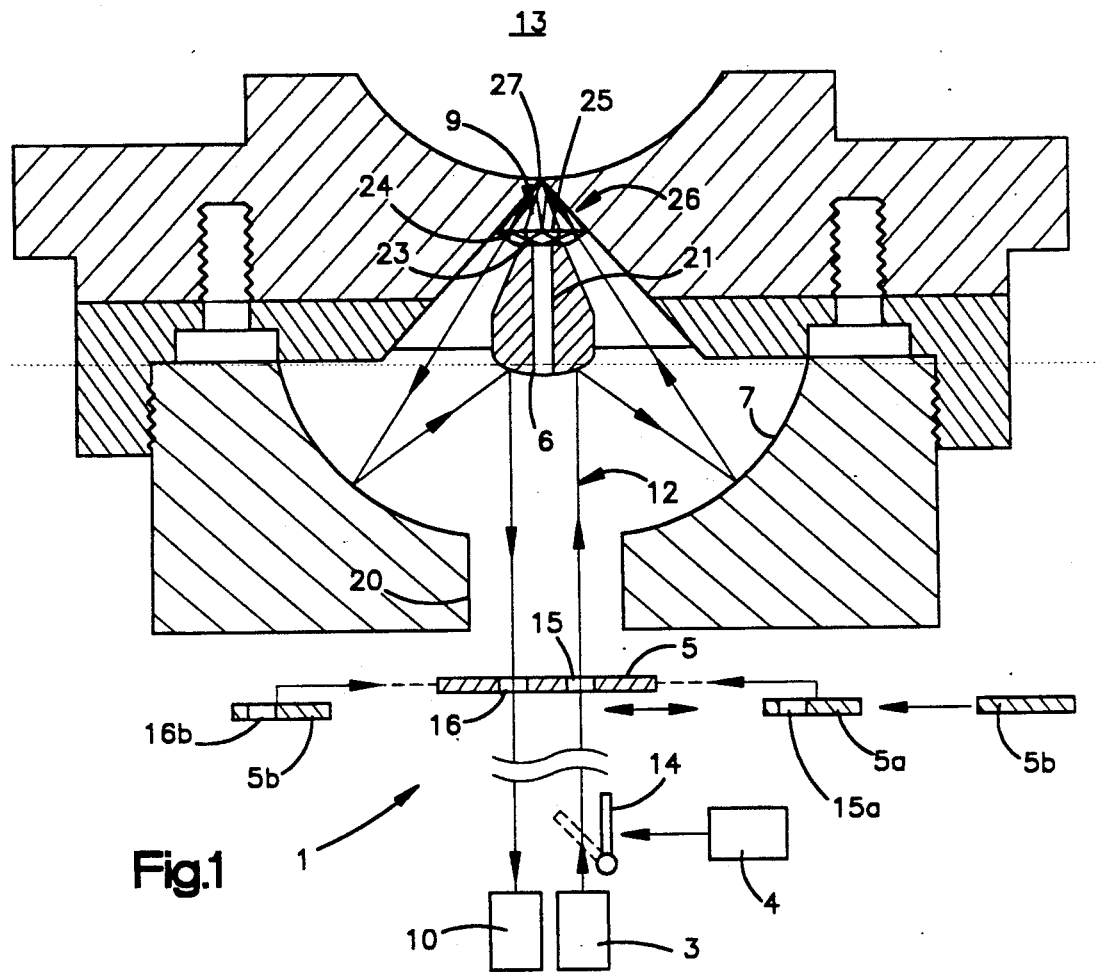
FIG. 1 is a vertical cross sectional elevation of a radiant energy spectroscopy system utilizing a diamond as a single bounce internal reflection element.

Turning now to the drawings and initially to FIG. 1, the radiant energy spectroscopy system of the present invention is indicated generally at 1. The system 1 may include a radiant energy source 3, a visible light source 4, a mask 5, an objective including a secondary mirror 6 and a primary mirror 7, a single bounce diamond IRE, indicated generally at 9, and a radiant energy detector 10.

The radiant energy source 3 directs the selected form of non-visible energy, preferably infrared energy, along the optical path, indicated generally at 12, of the system. The radiant energy supplied by radiant energy source 3 is used to analyze the sample, which in this case is a fluid 13 contained within a reaction chamber.

The radiant energy source 3 may be alternately used with the visible light source 4. A conventional switch mirror 14 can be pivoted between two positions alternately to direct either radiant energy or visible light along optical path 12. In the full line position shown in FIG. 1, mirror 14 allows radiant energy to pass through the spectroscopy system. When pivoted to the dotted line position shown in FIG. 1, the switch mirror 14 is positioned to direct visible light along the optical path of the spectroscopy system. This visible light can be viewed through conventional eye pieces to assist in setting up the optical system for specific analytical tests of the sample 13.

In this regard, various tests can be established by using different masks 5 or other optical elements. As illustrated in FIG. 1, a mask 5 having an inlet opening 15 and an outlet opening 16 is positioned in the optical path 12. As illustrated, the inlet opening 15 and outlet opening 16 are positioned equi-distant from the centerline through the optical system allowing ATR studies to be performed. With openings of limited size in the mask 5, only selected portions of the generally hemispherically shaped wavefront either enters or leaves the objective and IRE portion of the system.

To perform other studies, a different mask or masks can be used. For example, an inlet mask 5A having an inlet opening 15A can be positioned along the incident portion of the optical path to allow radiant energy to pass through inlet opening 15A. An outlet mask 5B having an outlet opening 16B can be selectively positioned in the reflected portion of the radiant energy path. Since inlet opening 15A and outlet opening 16B are unequally spaced from the center line of the optical system, scattering studies on sample 13 can be performed. It will be understood that numerous combinations of masks having openings of various widths, lengths, configurations and radial positions can be selectively mixed and matched to perform numerous ATR spectrographic studies. Other optical elements, such as a lens or lenses, may be used in place of the mask(s).

When visible light is being used, masks 5 can be selectively used, eliminated entirely, or replaced by a different optical element For example, a lens 5B may be positioned in the optical path of the system for focusing the light as required for the analytical test(s) or set up procedures(s) being performed.

The primary mirror 7 has an opening 20 positioned along the center line thereof to allow radiant and visible energy to pass therethrough in either direction. The secondary mirror 6 of the objective includes a bore 21 through the body thereof. The bore 21 is positioned along the center line of the secondary mirror 6 and allows visible light to pass therethrough to single bounce IRE diamond 9.

Figure 2:
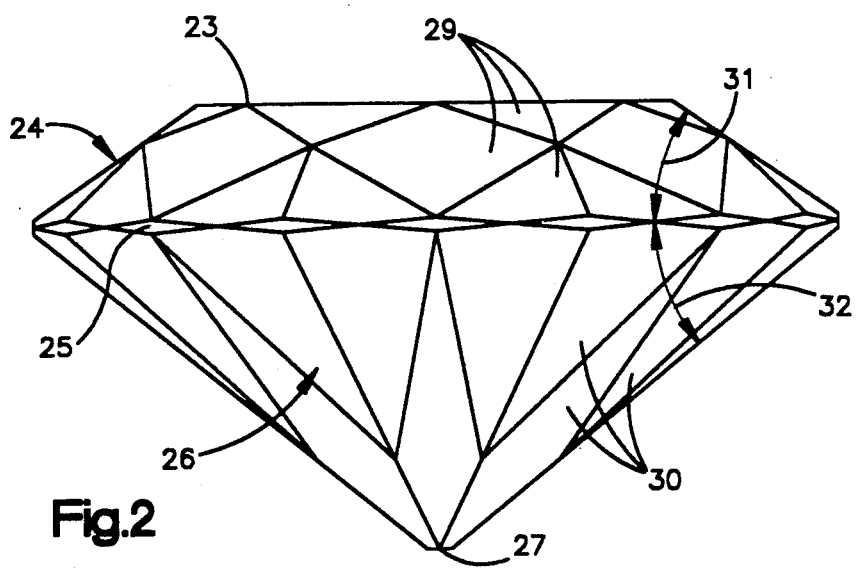
FIG. 2 is an elevation of a brilliant diamond used as an IRE in the present invention.
Figure 3A:
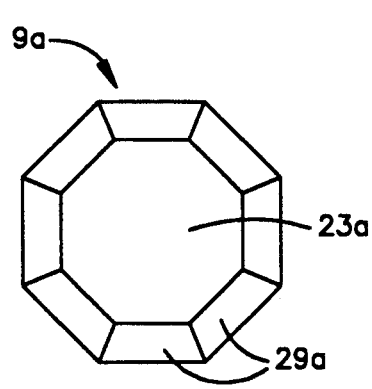
FIGS. 3A and 3B are top plan and front elevations of a Drukker standard diamond utilized as a single bounce IRE in the present invention.

As best shown in FIGS. 1 and 2, the diamond IRE 9 includes a table 23, a crown portion, indicated generally at 24, a girdle 25, a pavilion portion, indicated generally at 26, and a culet 27. The diamond 9 shown in FIG. 2 is a standard cut brilliant, or modified brilliant diamond. The table and culet are many sided and can be considered generally round in configuration. This diamond 9 includes table facets 29 and pavilion facets 30. The crown angle 31 is in the range of 30° to 40°, with a preferred angle of 34]° and the pavilion angle 32 is in the range of 25° to 45°, with a preferred pavilion angle of approximately 45°.

As shown in FIG. 1, the table surface 23 is positioned in abutment against the top surface of the body for secondary mirror 6, the pavilion portion 26 is sealed to the conical surface defined by the opening in the bottom wall of the reaction chamber, and the culet 27 is positioned in contact with the sample 13. In this embodiment, the radiant energy enters through and leaves from the crown portion 24 of diamond 9.

Figure 7:
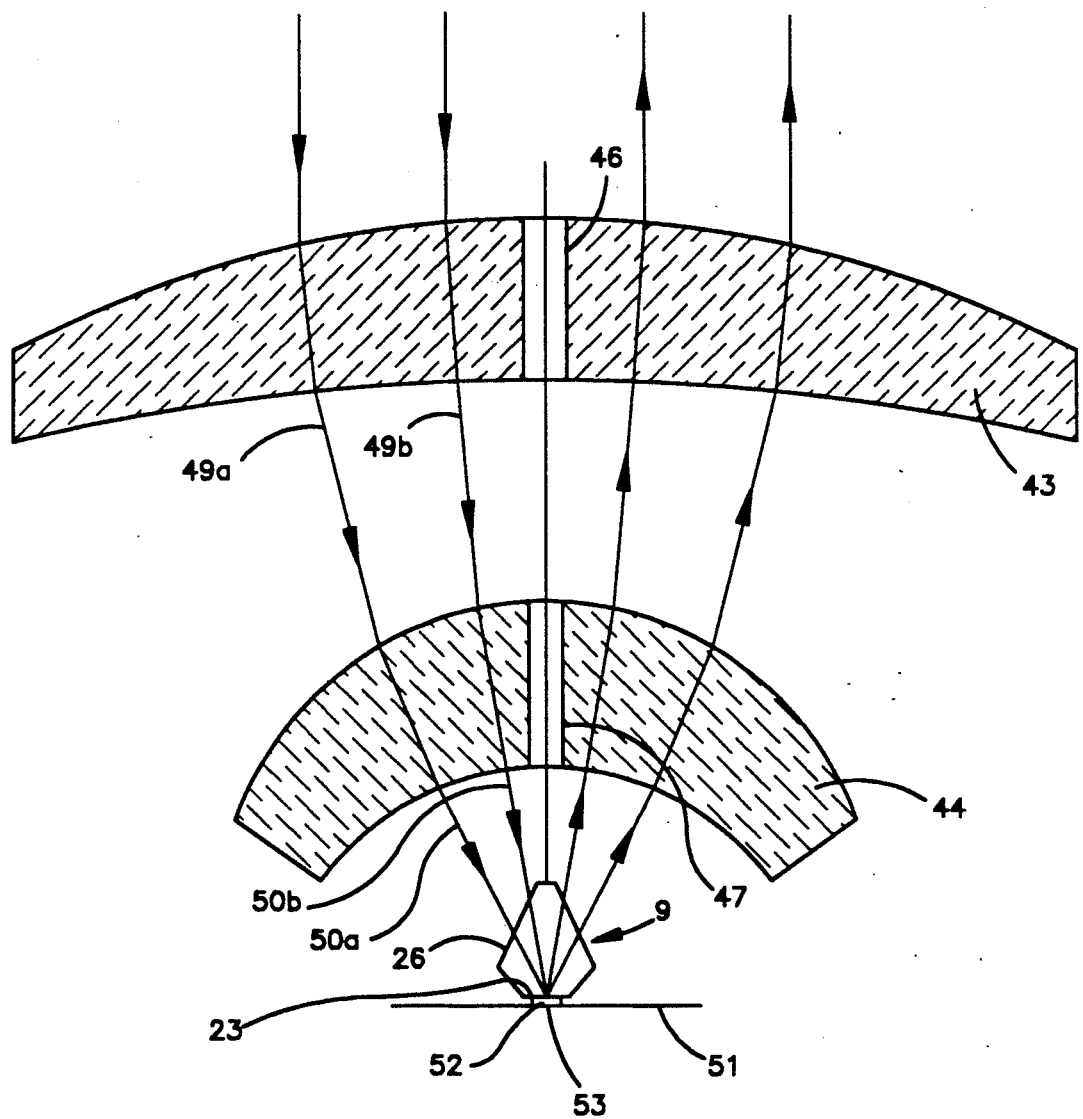
FIG. 7 is a schematic elevation of a radiant energy spectroscopy system utilizing refractive lenses and a single bounce diamond IRE.

It will be appreciated that the single bounce IRE diamond 9 could also be used in inverted fashion as shown for example in FIG. 7. If inverted in FIG. 1, the culet surface 27 would contact the body of secondary mirror 6, the crown portion 24 would be sealed to the substantially conical surface defined by the inlet opening in the bottom wall of the reaction chamber and the table surface 23 would be in contact with the sample 13. If so mounted, the radiant energy would enter through and leave from the pavilion portion 26 of diamond 9. In either event, the diamond IRE is hard, strong and chemically resistive to the sample and provides optical clarity.

It will be appreciated that other standard anvil cut diamonds or specially cut diamonds could be used as a single bounce, diamond IRE as illustrated for example in FIGS. 3 through 6. For example, in FIGS. 3A and 3B, a conventional anvil cut Drukker standard diamond 9A is shown as a possible IRE element. The table 23A and culet 27A are generally octagonally shaped. The crown portion 24A has eight table facets 29A and eight pavilion facets 30A. The girdle 25A has a larger height than the girdle 25 of the brilliant or modified brilliant cut diamond. The crown angle 31A is in the range of 35°–55°, with a preferred angle of 45°, and the pavilion angle 32A is in the range of 30°–40°, with a preferred angle of 35°.

Figure 4A:
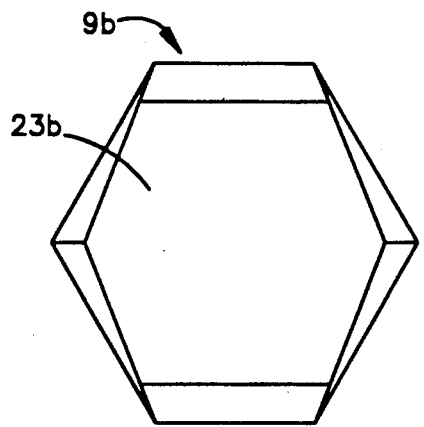
FIGS. 4A and 4B are plan and front elevation views of a specially cut diamond for use as a single bounce IRE.
Figure 3B:
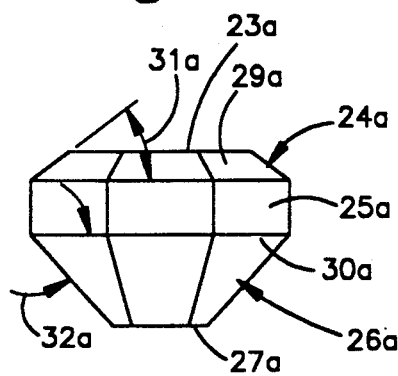
Figure 4B:
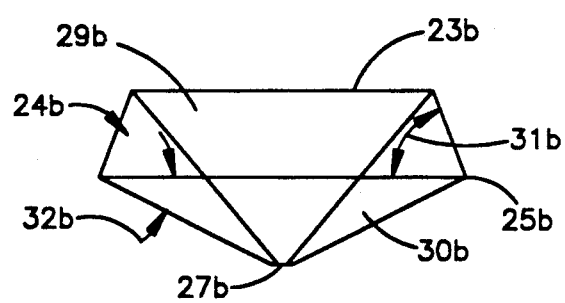

Turning now to a specially cut diamond 9B as shown in FIGS. 4A and 4B, the table 23B and culet 27B are generally hexagonal in shape. The crown portion 24B has six table facets 29B, while the pavilion portion 26B has six pavilion facets 30B. The crown angle 31B is in the range of 35°–55°, with a preferred angle of 45°, and the pavilion angle 32B is in the range of 30°–40°, with a preferred angle of 35°.

As shown in FIG. 4B, the culet 27B is extremely small. A diameter of 10 microns or less for the culet, when used as the sample contacting surface, is preferred when ultramicroscopy experiments are being performed. The size of the overall diamond is preferably minimized as well, with the largest dimension, such as the diameter in FIG. 4B, being less than four millimeters. The size of the single bounce diamond IRE 9 should be kept as small as possible for the particular analysis being performed. A smaller single bounce diamond IRE will result in less distortion of the image carried by the optical system, which distortion may result from the radiant energy passing through either the table facets or pavilion facets.

Figure 5:
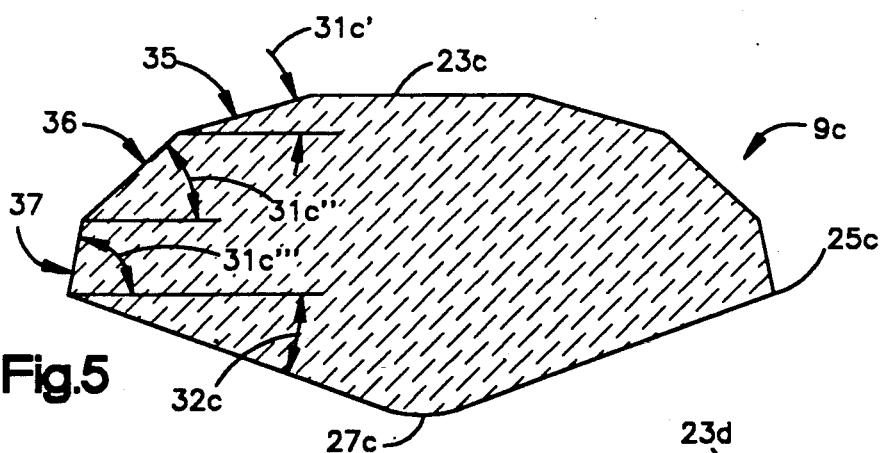
FIG. 5 is a vertical cross sectional of a specially cut diamond for use as a single bounce IRE.

Turning now to FIG. 5, a specially cut single bounce, diamond IRE 9C is illustrated. Such diamond 9C includes a table 23C and a culet 27C. The table and culet can be flat or curved. For example, a truncated portion of a sphere could be utilized to form either the table 23C or the culets 27C, or both.

In addition, the crown portion includes three different sections of table facets or surfaces, indicated generally at 35, 36 and 37. Each of the crown portion surfaces 36, 36 and 37 can be cut to include a plurality of faces, to include a portion of truncated cone, or to include a portion of a truncated sphere. In fact, the preferred angles and faces are selected to best approximate a spherical surface. When cut with facets, the number of facets in each of the sections can be increased and the size of the facets correspondingly decreased to approximate a spherical surface. Each of the facets is thus nearly perpendicular to a somewhat spherical wavefront created by the system optics. While three separate crown angles are provided in the diamond embodiment shown in FIG. 5, it will be appreciated that more or less crown angles may be provided as required by the application or use.

The diamond IRE 9C has a pavilion portion cut as a frusto conical portion, a frusto spherical portion or a multi-faceted portion. The pavilion angle 32C of diamond 9C is in the range of 30°–40°, with a preferred angle of 35°.

Figure 6:
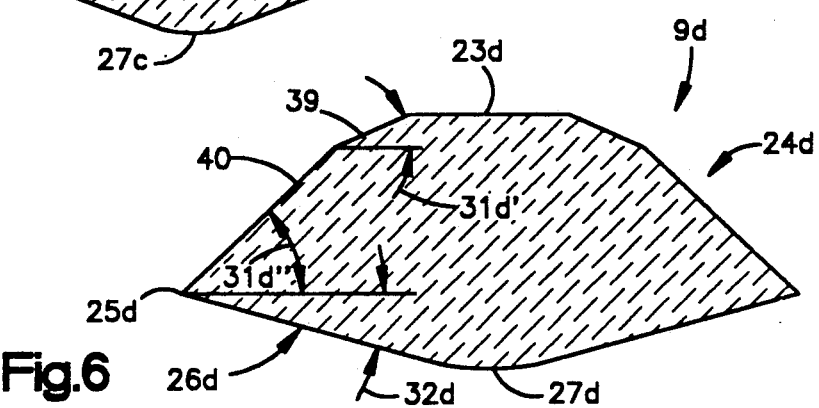
FIG. 6 is yet another vertical cross section of a specially cut diamond utilized as a single bounce IRE.

As yet another specially cut embodiment, diamond 9D of FIG. 6 includes a generally flat table 23D and a curved culet 27D. The crown 24D of diamond 9D includes two portions 39 and 40 which may be curved (for example, frusto conical or frusto spherical) or multi-faceted. The crown portion 24D has a first crown angle 31D' and a second crown angle 31D". The crown portion is again cut with preferred angles, and facets to approximate a spherical surface.

The pavilion portion 26D can be cut to be either curved or multi-faceted. The pavilion portion could also be cut to have a plurality of sections with different pavilion angles.

Applicant prefers to use a standard anvil cut diamond as a single bounce IRE for the spectroscopy system of the present invention, with such standard anvil cuts being shown, for example, in FIGS. 2 and 3. However, the present invention also contemplates the use of specially cut diamonds as single bounce IRE elements as may be required for specific spectroscopic or ultramicroscopic applications.

With respect to the operation of the system of FIG. 1 utilizing, for example, one of the diamonds shown in FIGS. 2 through 6, in the radiant energy analysis mode, the radiant energy passes through inlet opening 15 in mask 5, is sequentially reflected off secondary mirror 6 and primary mirror 7, passes through one half of crown portion 24 of diamond 9, is reflected only one time off culet 27, passes back through crown portion 24, is sequentially reflected off primary mirror 7 and secondary mirror 6, and passes through outlet opening 16 in mask 5 to detector 10. Some radiant energy will be absorbed by the sample 13 (typically liquid or solid phase). The detector can characterize the sample contained within the reaction chamber based upon radiant energy absorbed thereby.

In the viewing mode, incident visible light from source 4 will be refracted through lens 5B, will pass through bore 21 in the body of secondary mirror 6, will pass through table 23 of diamond 9, will then be reflected off culet 27, will sequentially pass through table 23 and bore 21, and will be refractively passed through lens 5B to a conventional eyepiece for operator viewing. Other applications for a single bounce diamond IRE and other orientations of that diamond IRE are contemplated.

For example, in FIG. 7, the objective of the system can include a refractive lens or lenses. As shown, the system of FIG. 7 includes a first refractive lens 43 and a second refractive lens 44. The first refractive lens 43 includes a first central bore 46, and the second refractive lens 44 includes a second central bore 47.

The incident radiant energy passing through first lens 43 is bent or refracted as schematically indicated by the incident optical paths 49A and B and is again bent or refracted by second refractive lens 44 as schematically indicated by the incident radiant energy paths 50A and B. The refractive lenses 43 and 44 are selected to focus the incident radiant energy at the sample plane 51.

In the embodiment shown in FIG. 7, a solid sample 52 has one surface thereof contacted by the table 23 of diamond 9. The hardness of the diamond and also the potentially small size of the culet allows significant pressure to be applied to the solid sample 52 to improve the spectroscopic analysis.

As shown in FIG. 7, the incident radiant energy passes through the pavilion portion 26 of the diamond to reach the table 23. The radiant energy is reflected one time (single bounce) off table 23 and passes through the other half of the pavilion portion 26 of diamond 9. The reflected radiant energy then sequentially passes through second refractive lens 44 and first refractive lens 43 on its way to detector 10.

In this case, the solid sample 52, which rests upon sample platform 53, is analyzed or characterized by the radiant energy absorbed. The diamond 9 in FIG. 7 is shown in inverted orientation relative to the diamond illustrated in FIG. 1.

In the viewing mode of operation, the refractive lenses 43 and 44 forming the objective of the system shown in FIG. 7 have the visible light pass through bores 46 and 47 for observation by the operator. The objective shown in FIG. 7 can be used with masks or other optical elements to perform selected analytical tests.

It will be apparent from the foregoing that changes may be made in the details of construction and configuration without departing from the spirit of the invention as defined in the following claims.

We claim:

1. A radiant energy spectroscopy system comprising:
   a source of radiant energy;
   a multi-faceted diamond as an internal reflection element;
   a sample in contact with one sample contacting surface of the diamond; and
   an optical system to direct the radiant energy to and from the diamond for a single internal reflection off the sample contacting surface of the diamond.

2. The radiant energy spectroscopy system of claim 1 wherein the optical system is a fully reflective mirror system.

3. The radiant energy spectroscopy system of claim 1 wherein the optical system includes at least one refractive lens.

4. A radiant energy spectroscopy system comprising:
   a source of radiant energy;
   a diamond as an internal reflection element, said diamond including a table, a crown, a girdle, a pavilion and a culet;
   a sample in contact with one sample contacting surface of the diamond; and
   an optical system to direct the radiant energy to and from the diamond for a single internal reflection off the sample contacting surface of the diamond.

5. The radiant energy spectroscopy system of claim 4 wherein the radiant energy enters and leaves the crown and the culet is the sample contacting surface.

6. The radiant energy spectroscopy system of claim 5 wherein the diamond is a modified brilliant cut having a crown angle in the range of 30°–40° and a pavilion angle in the range of 25°–45°.

7. The radiant energy spectroscopy system of claim 6 wherein the preferred crown angle is approximately 35° and the preferred pavilion angle is approximately 45°.

8. The radiant energy spectroscopy system of claim 5 wherein light enters and leaves the table of the diamond to permit viewing of the sample through the diamond.

9. The radiant energy spectroscopy system of claim 4 wherein the crown has at least two different portions having at least two different crown angles to approximate a spherical surface.

10. The radiant energy spectroscopy system of claim 9 wherein two crown angles are used, and a plurality of facets are used on each crown portion to have each of the same substantially perpendicular to the optical path of the system.

11. The radiant energy spectroscopy system of claim 9 wherein three crown angles are used, and a plurality of facets are used on each crown portion to have each of the same substantially perpendicular to the optical path of the system.

12. A radiant energy spectroscopy system comprising:
   a source of radiant energy;
   a diamond as an internal reflection element;

a sample in contact with one sample contacting surface of the diamond, the sample contacting surface being curved; and an optical system to direct the radiant energy to and from the diamond for a single internal reflection off the sample contacting surface of the diamond.

13. The radiant energy spectroscopy system of claim 4 wherein the diamond is of a standard anvil design wherein the crown has a plurality of table facets through which the radiant energy enters and leaves the diamond.

14. The radiant energy spectroscopy system of claim 13 wherein the largest dimension of the diamond is less than 4 millimeters.

15. A radiant energy spectroscopy system comprising:
   a source of radiant energy;
   a diamond as an internal reflection element;
   a sample in contact with one sample contacting surface of the diamond, the diamond including a crown and a pavilion, at least a portion of said crown being curved and at least a portion of said pavilion being conical; and
   an optical system to direct the radiant energy to and from the diamond for a single internal reflection off the sample contacting surface of the diamond.

16. A radiant energy spectroscopy system comprising:
   a source of radiant energy;
   a diamond as an internal reflection element;
   a sample in contact with one sample contacting surface of the diamond; and
   an optical system to direct the radiant energy to and from the diamond for a single internal reflection off the sample contacting surface of the diamond, the optical system including a detector for characterizing the sample and masks to select both the incident angle for the radiant energy entering the diamond or the reflected angle for the radiant energy reaching the detector from the diamond.

17. The radiant energy spectroscopy system of claim 4 wherein the radiant energy enters the leaves the pavilion and the table constitutes the sample contacting surface.

18. The radiant energy spectroscopy system of claim 4 wherein the largest dimension of the culet is less than 10 microns for ultramicroscopy analysis.

19. The radiant energy spectroscopy system of claim 15 wherein the largest dimension of the sampling surface is less than 10 microns.

* * * * *

UNITED STATES PATENT AND TRADEMARK OFFICE
CERTIFICATE OF CORRECTION

PATENT NO.   : 5,200,609
DATED        : April 6, 1993
INVENTOR(S)  : Sting, et al.

It is certified that error appears in the above-identified patent and that said Letters Patent is hereby corrected as shown below:

Col. 8, line 19: After the word "enters" delete [the] and insert therefor --and--.

Signed and Sealed this

Twenty-third Day of November, 1993

Attest:

BRUCE LEHMAN

Attesting Officer

Commissioner of Patents and Trademarks